US009724124B2

(12) United States Patent
Li et al.

(10) Patent No.: US 9,724,124 B2
(45) Date of Patent: Aug. 8, 2017

(54) DEVICES AND METHODS FOR CONTROLLING DEPTH OF INSERTION

(75) Inventors: Jamie Li, Lexington, MA (US); Jozef Slanda, Milford, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 974 days.

(21) Appl. No.: 13/568,848

(22) Filed: Aug. 7, 2012

(65) Prior Publication Data

US 2013/0041232 A1 Feb. 14, 2013

Related U.S. Application Data

(60) Provisional application No. 61/521,234, filed on Aug. 8, 2011.

(51) Int. Cl.
*A61B 1/32* (2006.01)
*A61B 17/34* (2006.01)
(Continued)

(52) U.S. Cl.
CPC ............ *A61B 17/3403* (2013.01); *A61B 1/04* (2013.01); *A61B 1/303* (2013.01);
(Continued)

(58) Field of Classification Search
CPC ....... A61B 1/303; A61B 17/42–17/425; A61B 17/02; A61B 1/32; A61B 17/3403
(Continued)

(56) References Cited

U.S. PATENT DOCUMENTS 2,672,859 A * 3/1954 Jones ..................... A61B 1/32
600/205
4,432,352 A * 2/1984 Wineland ............... A61B 17/42
600/218
(Continued)

FOREIGN PATENT DOCUMENTS

WO 2013/022957 A1 2/2013

OTHER PUBLICATIONS

International Search Report and Written Opinion for PCT Patent Application No. PCT/US2012/049975, mailed on Jan. 10, 2013, 14 pp.
(Continued)

*Primary Examiner* — Matthew Lawson
(74) *Attorney, Agent, or Firm* — Brake Hughes Bellermann LLP

(57) ABSTRACT

A medical device and a method for preparing a patient's body to receive a bodily implant are provided. The medical device includes a needle member configured to be inserted into a tissue layer. The needle member has a proximal end portion and a distal end portion. An adjustment member is coupled to the proximal end portion of the needle member. The adjustment member includes an adjustment screw and a nut for setting a predetermined depth of insertion of the needle member within the tissue layer. The adjustment member further includes an adjustment member support configured to provide a support to the adjustment screw and the nut. The adjustment member is configured to move between a first position and a second position with respect to the adjustment member support to limit insertion of the needle member within the tissue layer to the predetermined depth.

20 Claims, 16 Drawing Sheets

(51) Int. Cl.
*A61B 1/04* (2006.01)
*A61B 1/303* (2006.01)
*A61B 17/00* (2006.01)
*A61B 90/00* (2016.01)

(52) U.S. Cl.
CPC ............... *A61B 2017/00805* (2013.01); *A61B 2017/3405* (2013.01); *A61B 2090/061* (2016.02); *A61B 2090/062* (2016.02)

(58) Field of Classification Search
USPC ................... 604/117; 606/190; 600/184–246
See application file for complete search history.

(56) References Cited

U.S. PATENT DOCUMENTS

| | | | | |
|---|---|---|---|---|
| 4,585,438 | A * | 4/1986 | Makler | A61B 17/43 600/205 |
| 4,883,059 | A * | 11/1989 | Stedman | A61B 8/0833 600/437 |
| 5,380,292 | A | 1/1995 | Wilson | |
| 5,499,964 | A * | 3/1996 | Beck | A61B 1/0669 600/205 |
| 5,628,734 | A * | 5/1997 | Hatfalvi | A61B 17/3401 604/158 |
| 5,873,820 | A * | 2/1999 | Norell | A61B 1/32 600/220 |
| 5,897,590 | A | 4/1999 | Donovan | |
| 6,565,590 | B2 | 5/2003 | Kieturakis et al. | |
| 2001/0047151 | A1* | 11/2001 | Xian | A61B 17/3401 604/117 |
| 2004/0106846 | A1 | 6/2004 | Gellman | |
| 2006/0155169 | A1* | 7/2006 | Bastia | A61B 1/00105 600/199 |
| 2008/0009895 | A1* | 1/2008 | Pokomey | A61B 17/32002 606/185 |
| 2008/0091188 | A1 | 4/2008 | Gade | |
| 2011/0105850 | A1* | 5/2011 | Voegele | A61B 1/303 600/207 |
| 2011/0218444 | A1* | 9/2011 | Steffen | A61B 8/0833 600/461 |
| 2011/0230833 | A1* | 9/2011 | Landman | A61M 5/1456 604/117 |
| 2012/0130282 | A1* | 5/2012 | Galloway | A61M 25/0084 600/587 |

OTHER PUBLICATIONS

International Preliminary Report on Patentability for PCT Patent Application No. PCT/US2012/049975, mailed on Feb. 20, 2014, 9 pp.

* cited by examiner

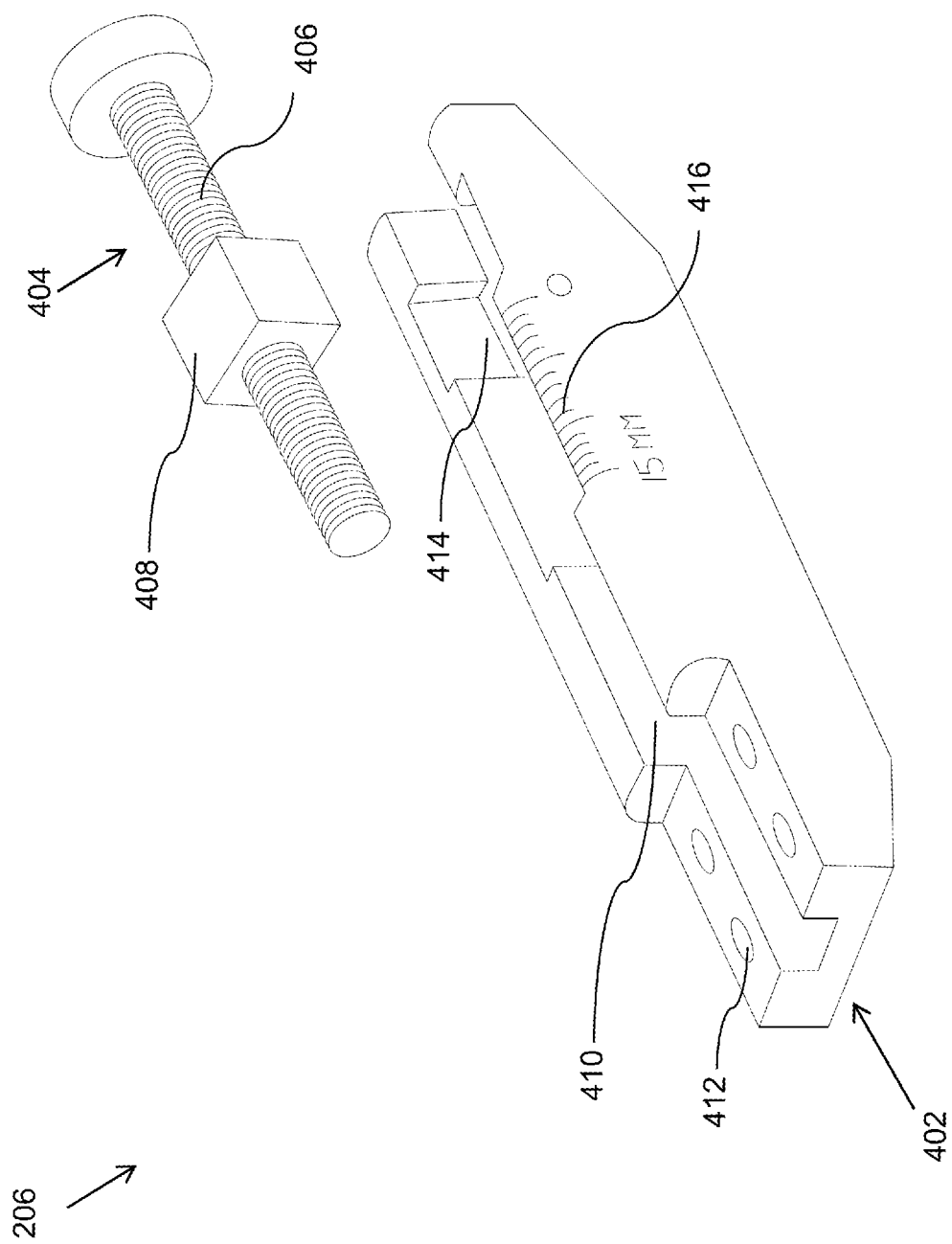

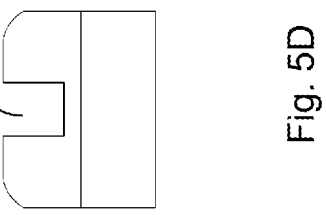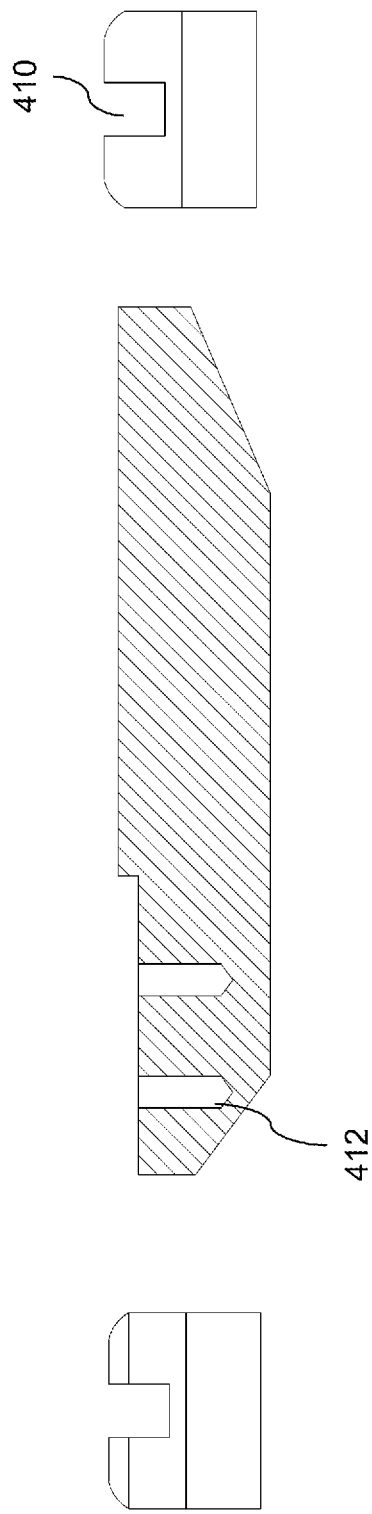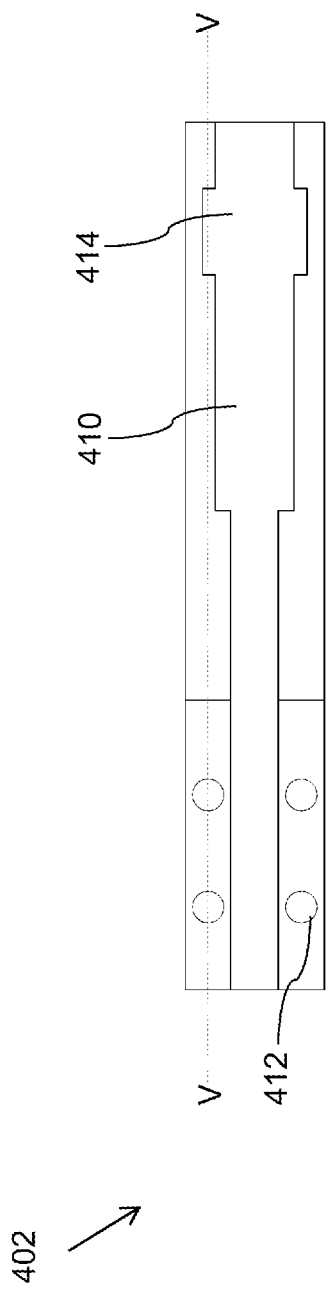

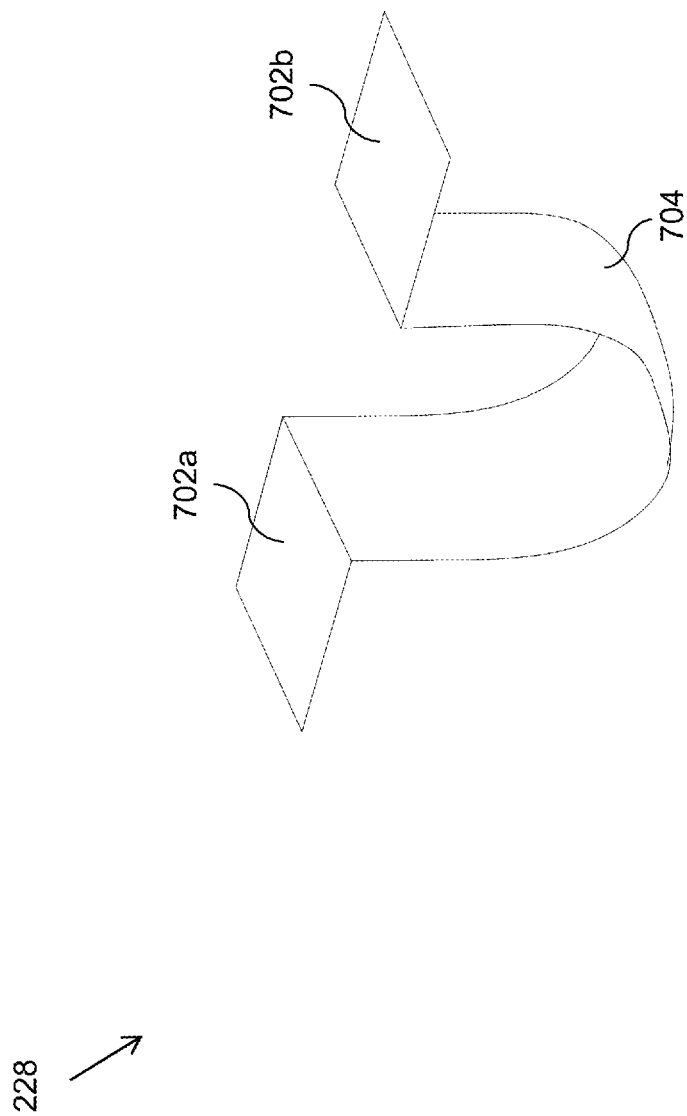

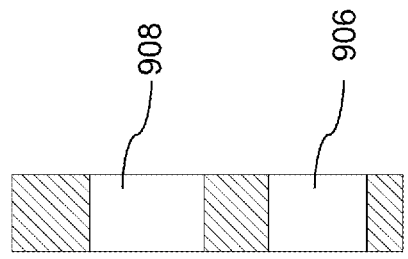
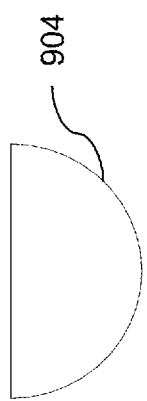
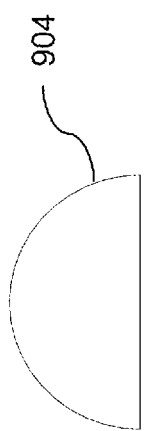

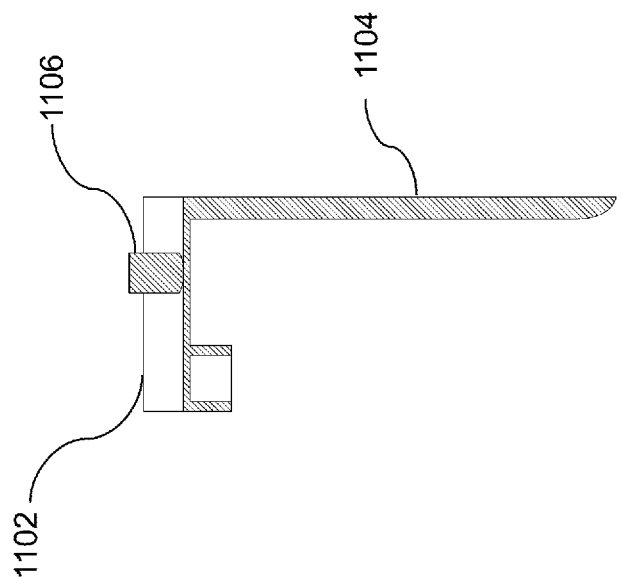
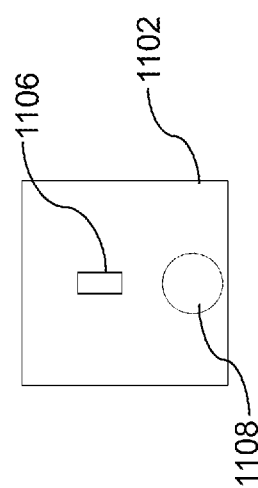
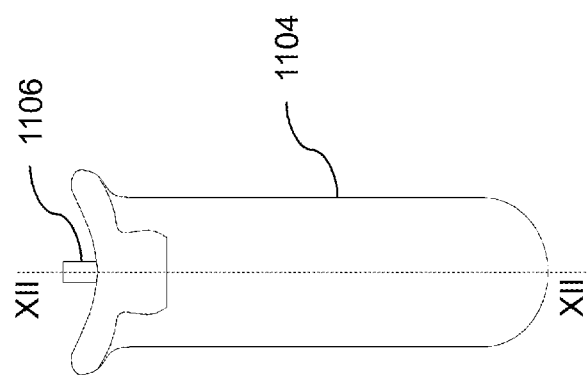

DEVICES AND METHODS FOR CONTROLLING DEPTH OF INSERTION

CROSS REFERENCE TO RELATED APPLICATION

This application is a Nonprovisional of, and claims priority to, U.S. Provisional Application No. 61/521,234, filed on Aug. 8, 2011, entitled "DEVICES AND METHODS FOR CONTROLLING DEPTH OF INSERTION", which is incorporated by reference herein in its entirety.

BACKGROUND

Field

The invention generally relates to medical devices and surgical procedures, and particularly medical devices and methods used for preparing a patient's body to receive a bodily implant.

Description of the Related Art

Mesh erosion can be a side effect after mesh repair, especially for female pelvic prolapse. Mesh, for example of an implant, erodes out of the tissues where it is originally implanted and thus, prevents curing/healing of tissues. One cause of mesh erosion may be that the tissue layer for mesh placement is incorrect.

In some procedures, an operator dissects the tissue layer and creates a pocket or space for placing the mesh, for example, in between the vagina and the bladder. The pocket/space is required because there is no space for mesh placement in a normal tissue. The operator identifies a position and makes an incision of about 2-3 cm in length inside the vagina. Then the operator inserts a finger to find way through the incision and keeps dissecting it till the layer is felt appropriate for creating the pocket. In this manner, the operator gets a hypothetical idea about the layer to be dissected for creating the pocket. In such cases, it is understood by the operator that dissecting the tissue layer too close to the vagina sides can cause mesh erosion through the vagina after placement of the mesh. Typically, identification of the erosion happens when a patient starts facing problems after one to three months of the mesh implant. On the contrary, it is also understood that dissection of the tissue layer at a deeper location may result in damage or perforation to the bladder. Therefore, an operator shall dissect at a proper depth for the prevention of the erosion and damage to the bladder.

In both the cases of close and deep dissection, the operator relies on his hypothesis and experience to identify the depth of the tissue layer for dissection. However, the operator cannot identify a fixed location within the tissue layer confidently, and therefore it results in mesh erosion some time after its placement.

In light of the above, there is a need for a medical device and a method that may assist the operator to conduct dissection at a predefined location. Thus, a medical device and a procedure that controls the depth of insertion to the predefined location inside the tissue layer are required.

SUMMARY

A medical device and a method for preparing a patient's body to receive a bodily implant are disclosed. The medical device includes a needle member configured to be inserted into a tissue layer. The needle member has a proximal end (the end that is closer to the operator) portion and a distal end portion (the end which is farther away from the operator). An adjustment member is coupled to the proximal end portion of the needle member. The adjustment member includes an adjustment screw and a nut for setting a predetermined depth of the needle insertion within the tissue layer. The adjustment member further includes an adjustment member support configured to provide a support to the adjustment screw and the nut. The adjustment member is configured to move between a first position and a second position with respect to the adjustment member support to limit insertion of the needle member within the tissue layer to the predetermined depth.

BRIEF DESCRIPTION OF THE FIGURES

The invention and the following detailed description of certain embodiments thereof may be understood with reference to the following figures:

FIG. 4 is an exploded perspective view of an adjustment member of a medical device, in accordance with an embodiment of the present invention.

FIG. 5A illustrates a front cross-sectional view of an adjustment member, in accordance with an embodiment of the present invention.

FIG. 5B illustrates a top view of an adjustment member, in accordance with an embodiment of the present invention.

FIGS. 5C and 5D illustrate left and right side views of an adjustment member, respectively, in accordance with an embodiment of the present invention.

FIG. 7 illustrates a perspective view of a bracket configured to couple a needle member with an insertion member, in accordance with an embodiment of the present invention.

FIG. 10A illustrates a top view of an upper portion of a lock assembly, in accordance with an embodiment of the present invention.

FIG. 10B illustrates a front cross-sectional view of an upper portion of a lock assembly, in accordance with an embodiment of the present invention.

FIGS. 10C and 10D illustrate right and left side views of an upper portion of a lock assembly respectively, in accordance with an embodiment of the present invention.

FIG. 12A illustrates a front cross-sectional view of a lower portion of a lock assembly, in accordance with an embodiment of the present invention.

FIG. 12B illustrates a top view of a lower portion of a lock assembly, in accordance with an embodiment of the present invention.

FIG. 12C illustrates a side view of a lower portion of a lock assembly, in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating female pelvic prolapse. However, the invention can be equally employed for other treatment purposes such as anal prolapse in males or females. As described below in various illustrative embodiments, the invention provides systems, methods, and devices employing an improved adjustment member configured to adjust and control the depth of insertion of a surgical needle within a tissue layer of a patient.

The term patient may hereafter be used for a person who benefits from the medical device or the methods disclosed in the present invention. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
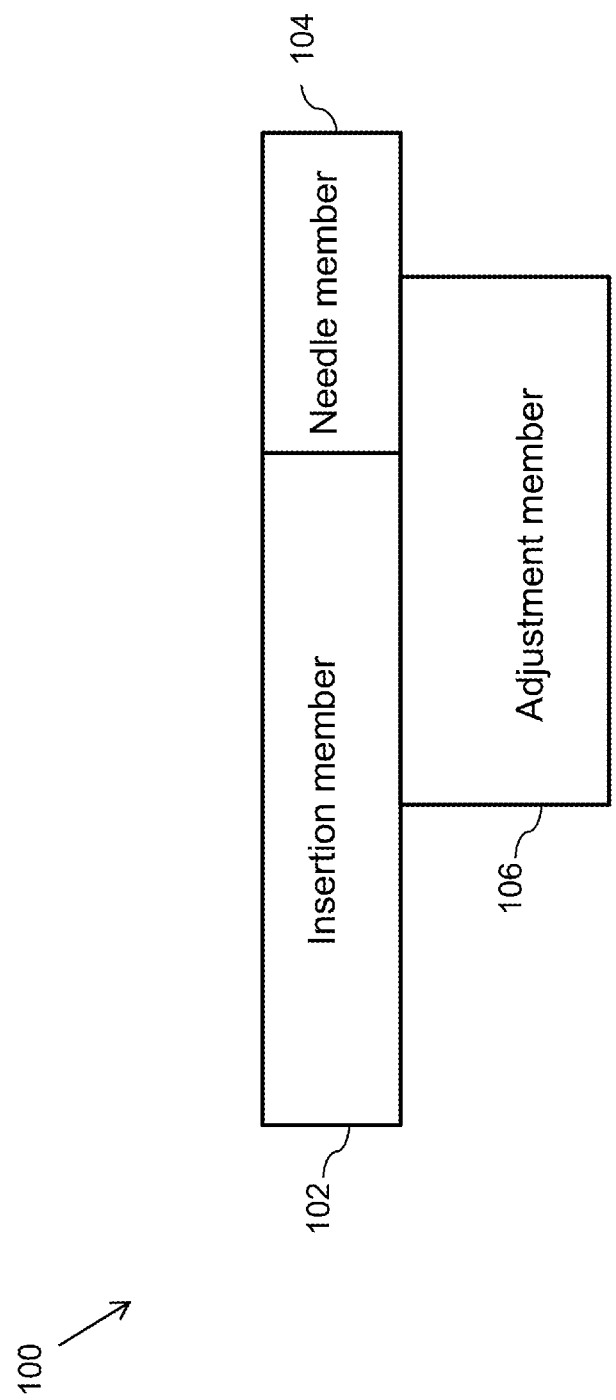
FIG. 1 is a schematic diagram of a medical device configured to prepare a patient's body for receiving a bodily implant, in accordance with an embodiment of the present invention.

FIG. 1 is a schematic diagram of a medical device 100 configured to prepare a patient's body for receiving a bodily implant (not shown). The bodily implant can be a mesh-based device, such as a sling, and the like, used in the treatment of fecal incontinence, urinary incontinence, prolapse, and other such disorders. The medical device 100 includes an insertion member 102, a needle member 104, and an adjustment member 106.

The insertion member 102 is configured to be inserted into a body opening such as a vagina, an anal canal, and the like. The insertion member 102 is capable of expanding the body opening once it is introduced in it. In some embodiments, the insertion member can include an expandable portion at its distal end such that the expandable member expands and causes the body opening to open. In some embodiments, the insertion member can be a dilator. In other embodiments, the insertion member can be a speculum. In some embodiments, the speculum can be a vaginal speculum configured for vaginal inspection/examination. In some other embodiments, the insertion member 102 can be any other type of an expandable device. In some embodiments, the insertion member 102 can include a set of blades or flaps that are configured to contact one another or get separated from one another, thereby allowing it to expand or collapse.

The needle member 104 is coupled to the insertion member 102 and configured to be inserted into a tissue layer. The needle member 104 has a proximal end portion and a distal end portion. In some embodiments, the needle member 104 can be a surgical needle configured to pierce through a patient's body during insertion. The needle member 104 can include a sharp tip portion provided at the distal end portion configured to pierce or puncture bodily tissues. In some embodiments, the needle member 104 can include a lumen that extends from the proximal end portion to the distal end portion of the needle member 104.

The adjustment member 106 is coupled to the proximal end portion of the needle member 104 and configured to limit advancement of the needle member 104 within the tissue layer to a predetermined depth. In some embodiments, the adjustment member 106 is configured to move between a first position and a second position with respect to the insertion member 102 to limit and adjust advancement of the needle member 104 within the tissue layer to the predetermined depth.

In accordance with various embodiments, the adjustment member 106 can include various types of mechanisms for controlling the depth of insertion within the tissue layer. In some embodiments, the adjustment member 106 includes an adjustment screw and a nut such that the movement of the adjustment screw between the first position and the second position can adjust the value of the predetermined depth accordingly. In accordance with various embodiments, the adjustment screw may include a lumen such that the needle member 104 can extend through it. The adjustment member 106 may further include a stopper to limit advancement of the needle member 104 within the lumen to a certain extent only. The needle member 104 may include a projection or any similar kind of an expanded portion such that the projection abuts the stopper when the needle member 104 extends through the lumen of the adjustment member 106, thereby limiting the advancement of the needle member 104 within the lumen. In some other embodiments, various other types of mechanisms for moving the adjustment member 106 between the first and the second positions can also be employed.

In accordance with various embodiments, the insertion member 102 (as described above) facilitates stretching of bodily tissues within the body opening. The stretched tissues assist in delivery and insertion of the needle member 104 to the predetermined depth such that a pocket or a space can be created at the desired location through various techniques such as hydro-dissection.

In some embodiments, the medical device 100 can also include a video camera configured to assist an operator in monitoring the tissue layers. The video camera can be coupled to the insertion member 102 or the needle member 104. The video camera can be configured to capture pictures or video clips from inside the body tissues and transmit them to an external terminal or viewing device controlled by the operator.

In some embodiments, the medical device 100 can also include a light source configured to assist the operator during insertion of the insertion member 102 and/or the needle member 104. The operator can view tissues inside the body and accordingly work on them comfortably. The light source can be coupled to the insertion member 102 or the needle member 104.

Figure 2:
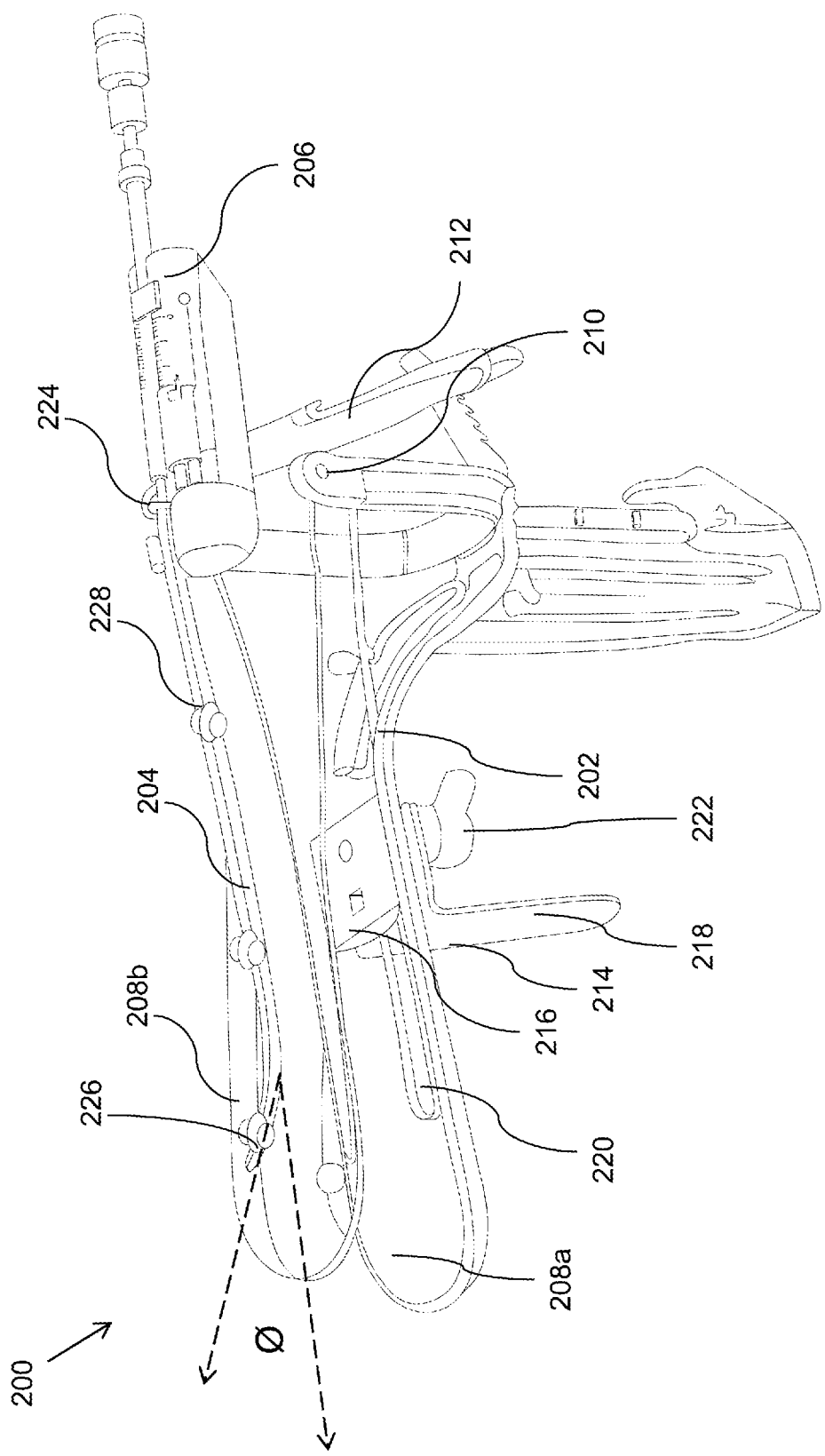
FIG. 2 is a perspective view of a medical device configured to prepare a patient's body for receiving a bodily implant, in accordance with an embodiment of the present invention.

FIG. 2 illustrates a perspective view of a medical device 200, in accordance with an embodiment of the present invention. The medical device 200 includes an insertion member 202, a needle member 204, and an adjustment member 206.

The insertion member 202 is configured to be inserted into a body opening such as a vagina, an anal canal, and the like. The insertion member 202 further includes two blade members—a first blade member 208a positioned on the lower side of the insertion member 202 and a second blade member 208b positioned on the upper side of the insertion member 202. The first blade member 208a and the second blade member 208b may be referred to as a lower blade member 208a and an upper blade member 208b, respectively. The first blade member 208a and the second blade member 208b (hereafter collectively referred to as blade members 208a and 208b) are movable with respect to one another through a hinged portion 210 fitted at a rear portion of the insertion member 202. In accordance with the movement of the blade members 208a and 208b, the insertion member 202 can have two configurations—a collapsed configuration and an expanded configuration. The expanded configuration is defined by the blade members 208a and 208b when separated from one another while the collapsed configuration is defined by the blade members 208a and 208b when contacting one another. In accordance with an exemplary scenario, FIG. 2 illustrates the expanded configuration of the blade members 208a and 208b. In some embodiments, the insertion member 202 can be a speculum. In some embodiments, the speculum can be a vaginal speculum configured for vaginal inspection/examination.

The insertion member 202 can further include a clamp 212 for allowing movement of the blade members 208a and 208b, thereby changing their configurations from a collapsed to an expanded one and vice versa. Additionally, an operator may set the distance between the blade members 208a and 208b at an intermediate position, which is between the completely collapsed and completely expanded configuration depending on the surgical and/or examination requirements. In some embodiments, the upper blade member 208b is movable to cause a relative movement with respect to the lower blade member 208a based on an adjustment through the clamp 212. In some other embodiments, the lower blade 208a member is movable to cause a relative movement with respect to the upper blade member 208b based on an adjustment through the clamp 212. In still other embodiments, both blade members 208a and 208b are movable with respect to one another to cause a relative movement. Thus, the operator can adjust the distance between the distal ends of the blade members 208a and 208b based on the surgical requirements.

Figure 3:
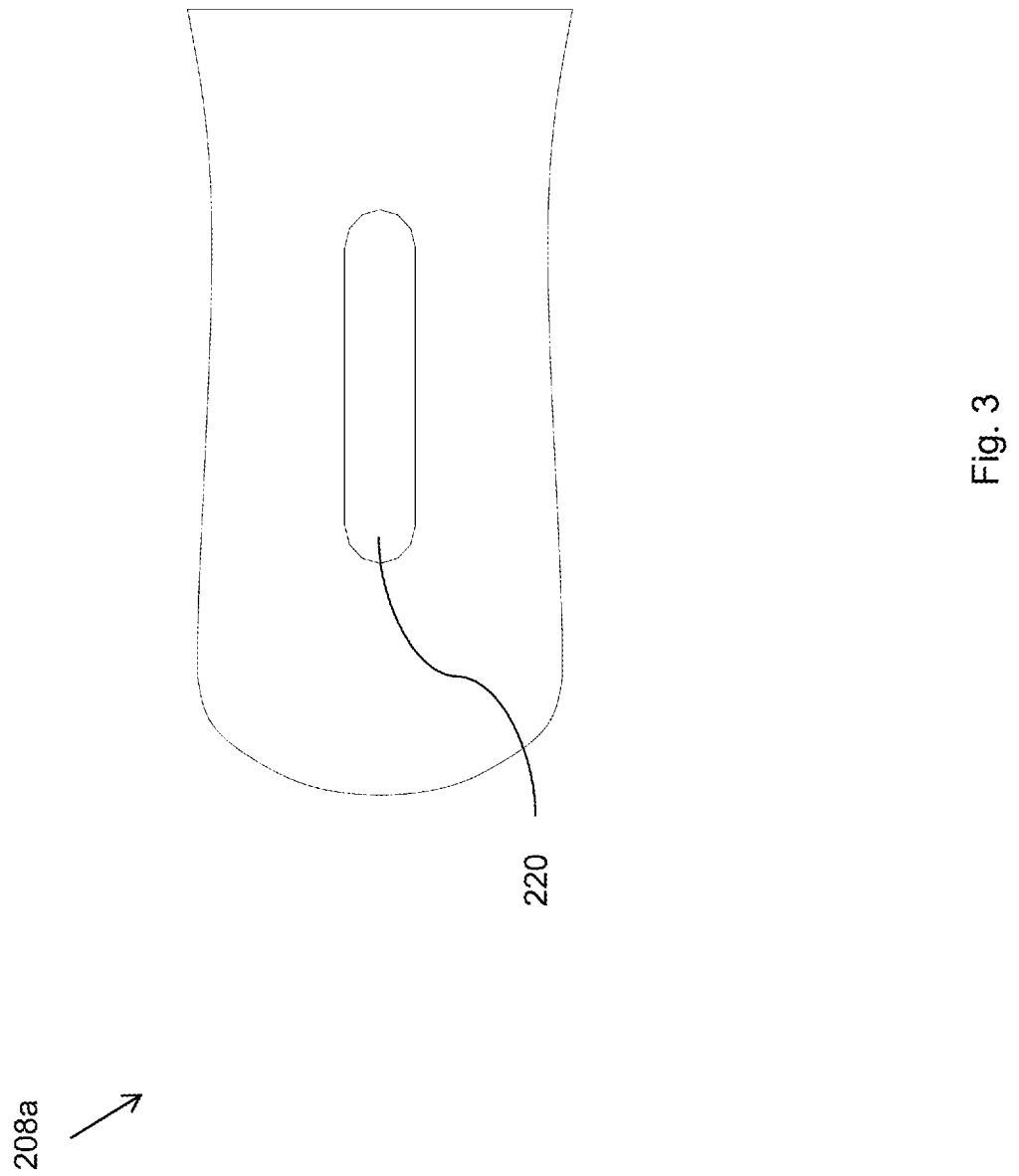
FIG. 3 is a top view of a portion of a lower blade member of the medical device of FIG. 2, having an opening thereto, configured to receive a lock assembly, in accordance with an embodiment of the present invention.

As shown in FIG. 2, the medical device 200 further includes a lock assembly 214 configured to limit and/or make adjustments to the depth of insertion of the insertion member 202 in a patient's body opening such as a vagina, anal canal, and the like. Therefore, by adjusting the lock assembly, the insertion member 202 goes into the body opening only to the desired depth. The lock assembly includes an upper portion 216 and a lower portion 218. The lock assembly 214 is fitted to the lower blade member 208a of the insertion member 202. The lock assembly 214 is further described in conjunction with FIGS. 9-12. In some embodiments, an opening 220 along a surface of the lower blade member 208a may be provided to clamp the lock assembly 214 fixedly. An enlarged illustration of the opening 220 is shown in FIG. 3. FIG. 3 illustrates a top view of a portion of the lower blade member 208a having the opening 220 configured to receive the lock assembly 214. In accordance with various embodiments, the opening 220 allows positional arrangement of the lower portion 218 (which is in the shape of a flap) of the lock assembly. For example, the lower portion 218 can be moved from one position to another through a knob 222 such that this movement adjusts the depth of insertion of the medical device 200 within the vagina or other body openings. The lower portion 218 limits insertion of the medical device 200 because it touches the external body of the patient and does not allow further insertion. The adjustment through the lock assembly tries to adjust the position of the lower portion 218 within the opening 220, thereby locking it for a set depth of insertion within the body opening.

The needle member 204 is coupled to the insertion member 202 and configured to be inserted into a tissue layer. The needle member 204 is coupled to the upper blade member 208b of the medical device 200 through a set of brackets at certain positions. Brackets similar to the bracket 228 are used to hold the needle member 204 with the insertion member 202.

The needle member 204 has a proximal end portion 224 and a distal end portion 226. In some embodiments, the needle member 204 can be a surgical needle configured to pierce a patient's body during insertion. The needle member 204 can include a sharp tip portion at the distal end portion 226 configured to pierce/puncture bodily tissues. In some embodiments, the needle member 204 can include a lumen defined across the length of the needle member 204 that extends from the proximal end portion 224 to the distal end portion 226.

The length of the needle member 204 extends along and is positioned under the upper blade member 208b. The distal end portion 226 of the needle member 204 comes out through an opening on the upper blade member 208b such that the needle member 204 protrudes upward the upper blade member 208b at the distal end portion 226.

The needle member 204 can have a variety of shapes and sizes depending on the surgical requirements. In accordance with various embodiments, various kinds of conventional surgical needles available can be used as the needle member 204 of the present invention.

In some embodiments, the needle member 204 is curved to a defined length at its distal end portion 226. The curved portion of the needle member 204 makes an angle Ø with respect to a distal end portion of the upper blade member 208b as shown in FIG. 2. In some embodiments, this angle can vary from 30 to 45 degrees. However, other angle values are also possible based on the curvature of the distal end portion 226 of the needle member 104, in accordance with other embodiments. In some embodiments, the curvature is directed toward the upper blade member 208b as shown in FIG. 2.

The adjustment member 206 is coupled to the proximal end portion 224 of the needle member 204 and configured to limit advancement of the needle member 204 within the tissue layer to a predetermined depth. In accordance with various embodiments, the adjustment member 206 can employ various types of mechanisms for adjusting the value of the predetermined depth. In some embodiments, the adjustment member 206 includes an adjustment screw and a nut such that the movement of the adjustment screw between a first position and a second position will adjust the value of the predetermined depth accordingly. In some other embodiments, various other types of mechanisms for moving the adjustment member 206 between the first and the second position can also be employed.

An exploded perspective view of the adjustment member 206 is illustrated in FIG. 4. As illustrated in FIG. 4, the adjustment member 206 includes an adjustment member support 402 and an adjustment screw-nut member 404. The adjustment screw-nut member 404 further includes a screw 406 and a nut 408. The adjustment screw 406 is configured to move between a first position and a second position with respect to the insertion member 202 or the adjustment member support 402 to limit the advancement of the needle member 204 to the predetermined depth within the tissue layer. The length and diameter of the screw 406 can vary based on the requirements. FIG. 4 illustrates an exemplary screw and nut, and it must be appreciated that various other kinds of conventionally used screws and nuts may be employed in the adjustment member 206 in accordance with various other embodiments.

In some embodiments, the adjustment member 206 can also include a stopper at the proximal end portion of the adjustment member 406. The stopper is configured to stop the needle member 204 from penetrating further from the predetermined depth. In some embodiments, the stopper may include a box like structure at the proximal end portion of the adjustment member 406 having a lumen therein. In some embodiments, the stopper can be head of the screw of the adjustment member 406. In some embodiments, the needle member 204 may include a projection (not shown) at its proximal end such that the needle member 204 is configured to advance through the lumen of the adjustment member 204 and the stopper during insertion. However, the projection of the needle member 608 abuts the stopper after the predetermined depth is reached such that the abutting controls the insertion to the predetermined depth only. The predetermined depth at which the projection abuts the stopper can be adjusted by the adjustment member 206 (based on the requirements) by moving the screw member to different positions with respect to the insertion member 204 using the nut.

The adjustment member support 402 includes a longitudinal recess 410 for receiving the adjustment screw-nut member 404 therein. A plurality of holes 412 may be provided on a distal end portion of the adjustment member support 402 to couple it with the insertion member 202 through fasteners such as screws, nails, bolts, and the like. A block or a rectangular recess 414 is provided on a proximal end portion of the adjustment member support 402 to receive the nut 408. In accordance with some embodiments, as illustrated in FIG. 4, the nut 408 can be a square nut. In some other embodiments, the nut 408 can have other shapes such as circular, hexagonal, pentagonal, and the like. The design of the recess 414 provided in the adjustment member support 402 for receiving the nut 408 can be modified based on the shape of the nut 408.

The different views of the adjustment member support 402 taken at different angles are illustrated in FIGS. 5A-5D. FIG. 5A illustrates a front cross-sectional view of the adjustment member support 402. FIG. 5B illustrates a top view of the adjustment member support 402. FIGS. 5C and 5D illustrate the left and right side views of the adjustment member support 402, respectively.

The adjustment member 206 further includes a scale 416 for locating a pre-settable numerical value of the predetermined depth adjusted by the adjustment screw-nut 404. In some embodiments the scale 416 includes markings or other visible or tactile indicia. The scale 416 can be calibrated such that the adjusted value indicates the predetermined depth of insertion of the needle member 204 within the tissue layers, as discussed above. As an exemplary scenario illustrated in FIG. 4, the scale 416 is calibrated to indicate the predetermined depth of insertion ranging between 0 mm and 15 mm. However, in certain other embodiments, the range can be varied.

Figure 6:
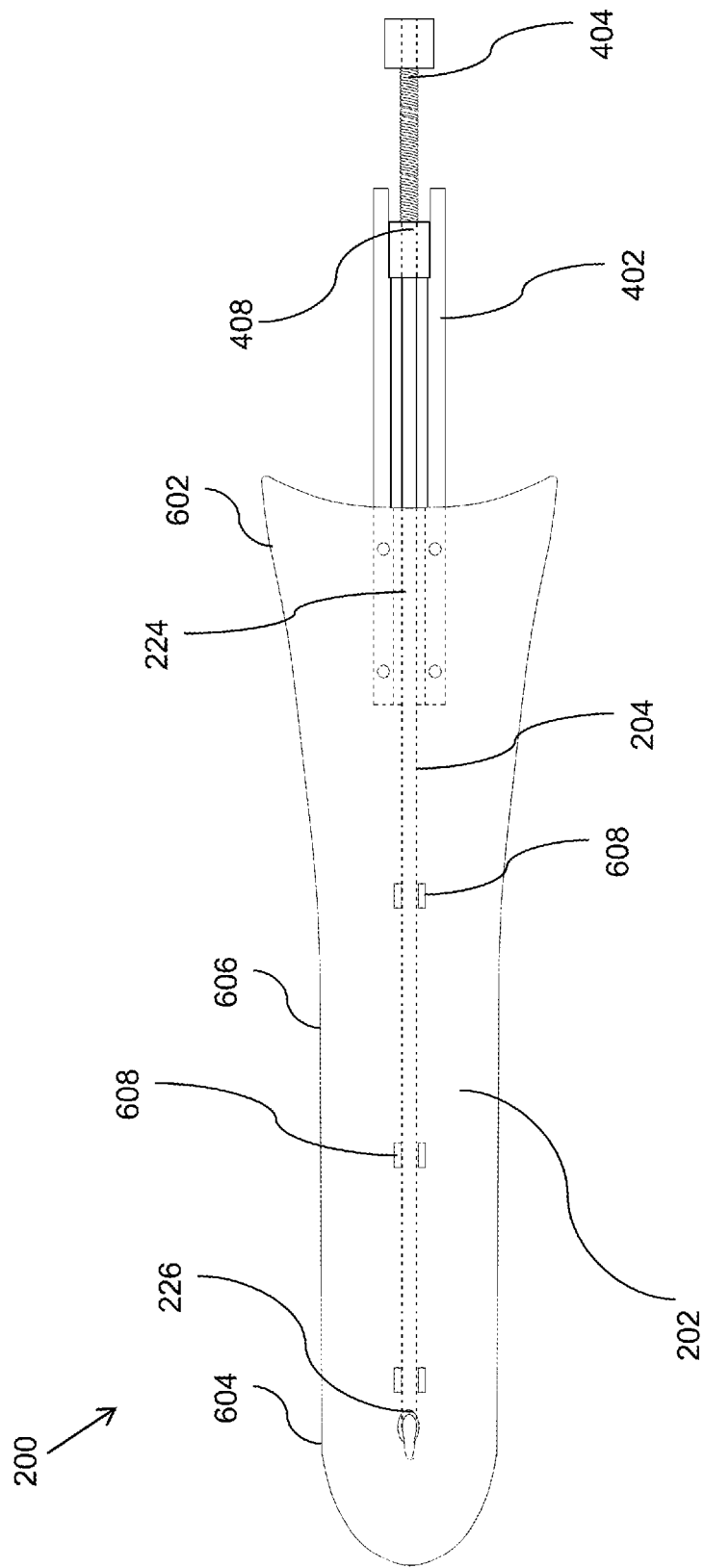
FIG. 6 illustrates a top view of a portion of the medical device of FIG. 2, in accordance with an embodiment of the present invention.

FIG. 6 illustrates a top view of a portion of the medical device 200 as illustrated in FIG. 2. The insertion member 202 includes a proximal end portion 602, a distal end portion 604, and a medial portion 606. FIG. 6 illustrates an exemplary design of the upper blade member 208b; however, other designs and shapes can also be employed in the present invention. As shown in this figure, the adjustment member 206 is coupled to the proximal end portion 602 of the insertion member 202. The needle member 204 that is placed below the upper blade member 208b is shown by dotted lines. A portion of the length of the needle member 204 sits into the recess of the adjustment member support 402. As illustrated, the distal end portion 226 of the needle member 204 comes outward through the opening provided on the upper blade member 208b.

Referring to FIGS. 2 and 6, the needle member 204 is coupled to the upper blade member 208b of the medical device 200 through a set of brackets at certain positions. Brackets similar to the bracket 228 are used to hold the needle member 204 with the insertion member 202.

A perspective detailed view of the bracket 228 is illustrated in FIG. 7. The bracket 228 includes two substantially rectangular and horizontal strips 702a and 702b, and a curved strip 704 extending between the two rectangular strips 702a and 702b. The curved strip 704 is configured to overlap a curved body surface of the needle member 204 while the rectangular strips 702a and 702b are configured to fit into the insertion member 202 for being coupled thereto using fasteners. In some embodiments, holes may be provided on the rectangular strips 702a and 702b of the bracket 228 to fasten them through screws, nails, bolts, and the like. A space is provided between the needle member 204 and the inner surface of the bracket 228 that is closer to the needle member 204 such that a relative movement of the needle member 204 is possible with respect to the bracket 228 during insertion. The brackets similar to the bracket 228 are fitted at defined spatial intervals along the length of the needle member 204. The illustrated bracket 228 is an exemplary fastener. A variety of other kinds of fasteners that are conventionally used can also be utilized to couple the needle member 204 with the insertion member 202.

Figure 8A:
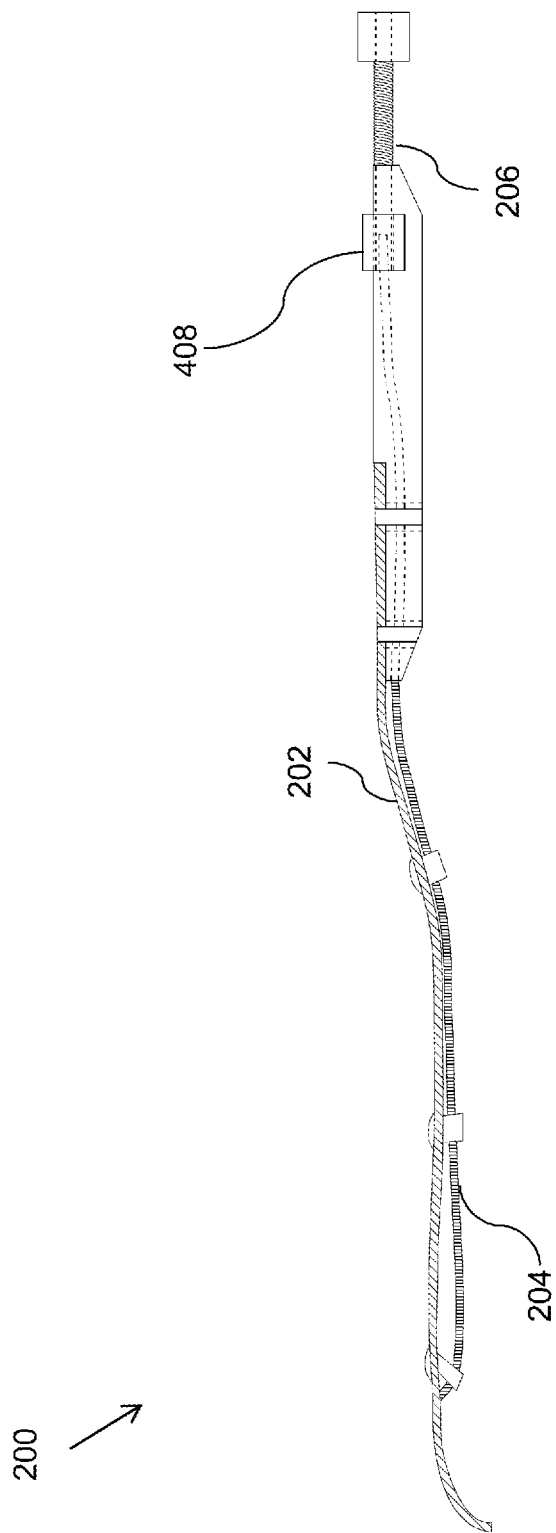
FIG. 8A illustrates a front view of a medical device, in accordance with an embodiment of the present invention.
Figure 8B:
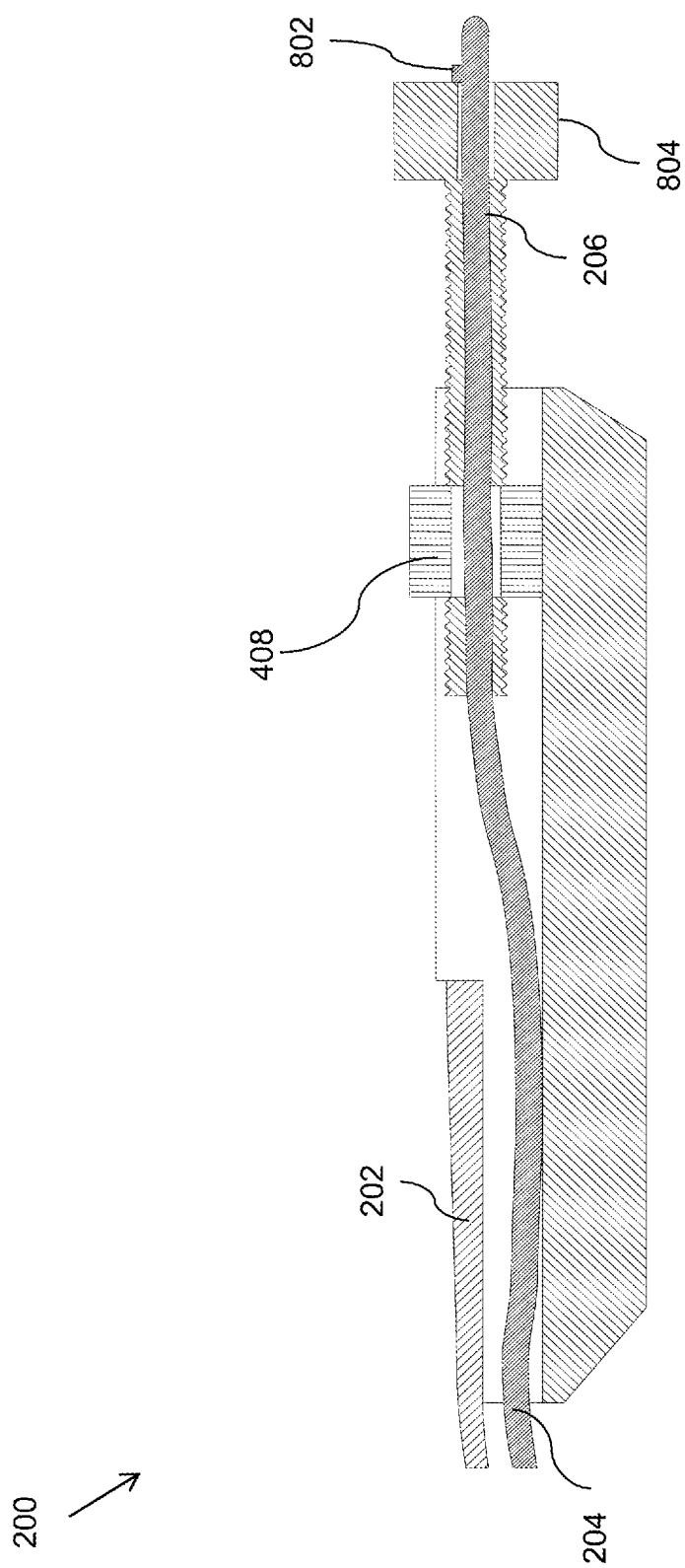
FIG. 8B illustrates an enlarged view of a portion of the medical device of FIG. 8A.

FIG. 8A illustrates a front view of the medical device 200, in accordance with an embodiment of the present invention. FIG. 8B illustrates an enlarged view of a portion of the medical device illustrated in FIG. 8A. Referring to FIGS. 8A and 8B now, the needle member 204 advances through the lumen of the adjustment member 204. However, a projection such as the projection 802 of the needle member 608 as shown in FIG. 8B abuts a stopper such as the stopper 804 after the predetermined depth is reached such that the abutting controls the advancement to a fixed distance only within the lumen. This has been further described in conjunction with FIGS. 2 and 4.

Figure 9:
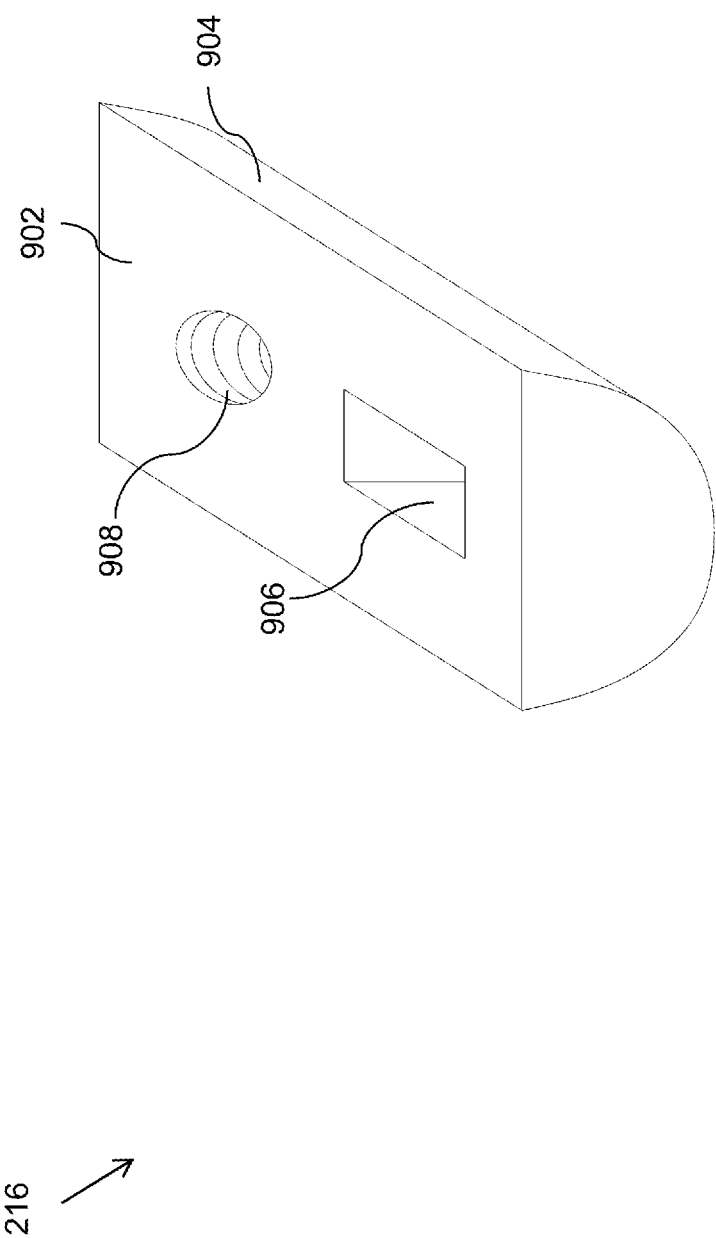
FIG. 9 illustrates a perspective of an upper portion of a lock assembly, in accordance with an embodiment of the present invention.

FIG. 9 illustrates a perspective view of the upper portion 216 of the lock assembly 214 as illustrated in conjunction with FIG. 2 in an assembled form. The upper portion 216 has a rectangular top surface 902 and a curved bottom surface 904 extending from the rectangular surface on both the sides. The upper portion 216 is further provided with a first opening 906 of the shape of a rectangular pass-through hole and a second opening 908 in the form of a circular pass-through hole. The first opening 906 and the second opening 908 of the upper portion 216 are configured to receive the lower portion 218 of the lock assembly 214 as illustrated in FIGS. 2 and 11.

The different views of the upper portion 216 taken along different angles are illustrated in FIGS. 10A-10D. FIG. 10A illustrates a top view of the upper portion 216 of the lock assembly 214. FIG. 10B illustrates a front cross-sectional view of the upper portion 216 of the lock assembly 214. FIGS. 10C and 10D illustrate the right and left side views of the upper portion 216 of the lock assembly 214. Although the upper portion 216 is illustrated with a specific design, it must be appreciated that other designs and shapes of the upper portion 216 are equally possible to define the present invention.

Figure 11:
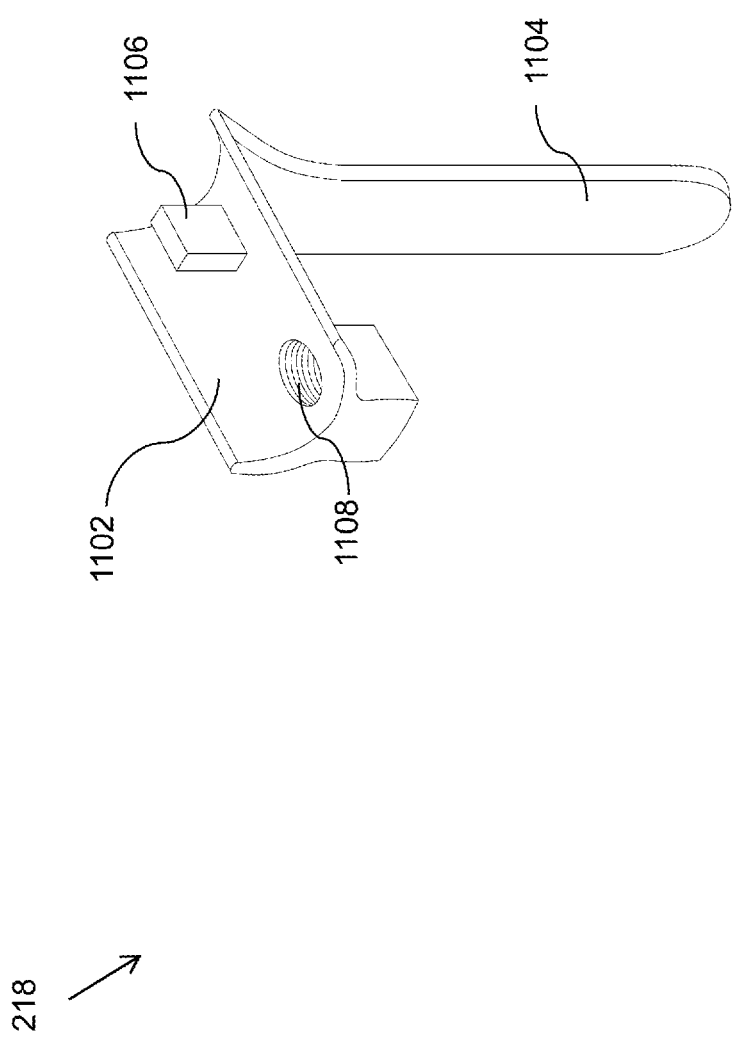
FIG. 11 illustrates a perspective view of a lower portion of a lock assembly, in accordance with an embodiment of the present invention.

FIG. 11 illustrates a perspective view of the lower portion 218 of the lock assembly 214. The lower portion 218 has a curved member 1102 and an arm member 1104 extending from the curved member 1102. The curved member 1102 is concave such that the curved surface of the upper portion 216, as illustrated in FIG. 9, can be fitted to the concave surface of the curved member 1102. The curved member 1102 further includes a projection 1106 configured to be fitted in the first rectangular opening 906 provided in the upper portion 1106, thereby assembling the upper and lower portions 1106 and 1108 fixedly. Additionally, a circular opening 1108 is provided in the curved member 1102 to receive a bolt, screw or any similar longitudinal member that forms a part of the knob 222 (not shown in FIG. 11) for making adjustments.

The different views of the lower portion 1108 taken along different angles are illustrated in FIGS. 12A-12C. FIG. 12A illustrates a front cross-sectional view of the lower portion 1108 of the lock assembly 1104. FIG. 12B illustrates a top view of the lower portion 1108 of the lock assembly 214. FIG. 12C illustrates a side view of the lower portion 1108 of the lock assembly 214. Although the lower portion 1108 of the lock assembly 214 is illustrated with a specific design, it must be appreciated that other designs and shapes of the lower portion 1108 are equally possible to define the present invention. In accordance with various embodiments, the lock assembly 214 is configured to limit and/or make adjustments to the depth of insertion of the insertion member 202 in the patient's body opening such as a vagina, anal canal, and the like. Therefore, the insertion member 204 is inserted only to a defined depth inside the body opening once the insertion member is locked through the lock assembly 214.

Figure 13:
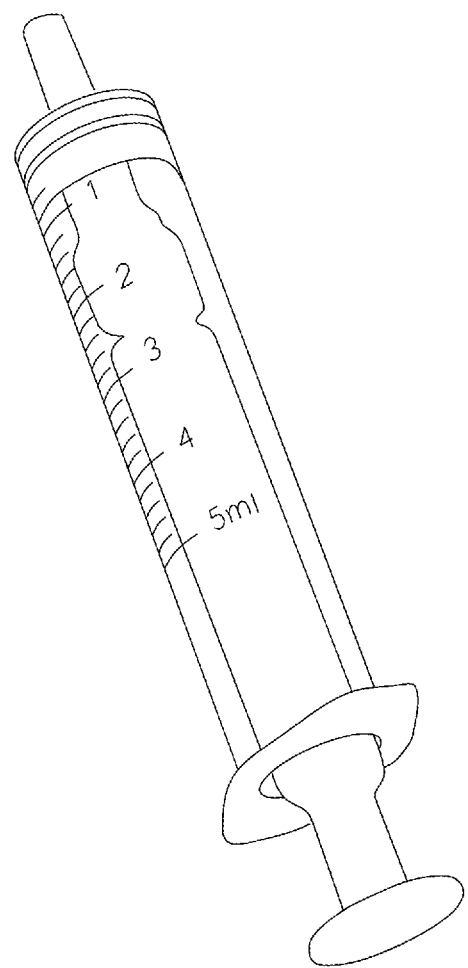
FIG. 13 illustrates a syringe configured to be coupled to a medical device, in accordance with an embodiment of the present invention.

FIG. 13 illustrates a syringe 1300 configured to be coupled to a needle member such as the needle member 104 or 204 (as described in conjunction with FIGS. 1 and 2, respectively). In some embodiments, the syringe 1300 is removably coupled to the needle member 104 or 204 such that the needle member 104 or 204 can receive standard sized syringes. In some other embodiments, the syringe 1300 is permanently coupled to the needle member 104 or 204 and the syringe 1300 forms a part of the medical device 100 or 200 described in conjunction with FIGS. 1 and 2, respectively.

The syringe 1300 contains a solution. In some embodiments, the solution is a saline solution. The syringe 1300 is configured to inject the solution through the insertion member such as the insertion member 102 or 202 (as described in conjunction with FIGS. 1 and 2, respectively). The syringe 1300 aids in creation of a pocket in a tissue layer proximate a distal end portion of the insertion member 102 or 202. In some embodiments, the pocket is created in the tissue layer by the hydro-dissection technique. The syringe 1300 as illustrated in FIG. 13 is shown for illustrative exemplary purposes, and it must be appreciated that various other conventional designs and types of syringes available may be employed for dissecting the tissue layer.

Figure 14:
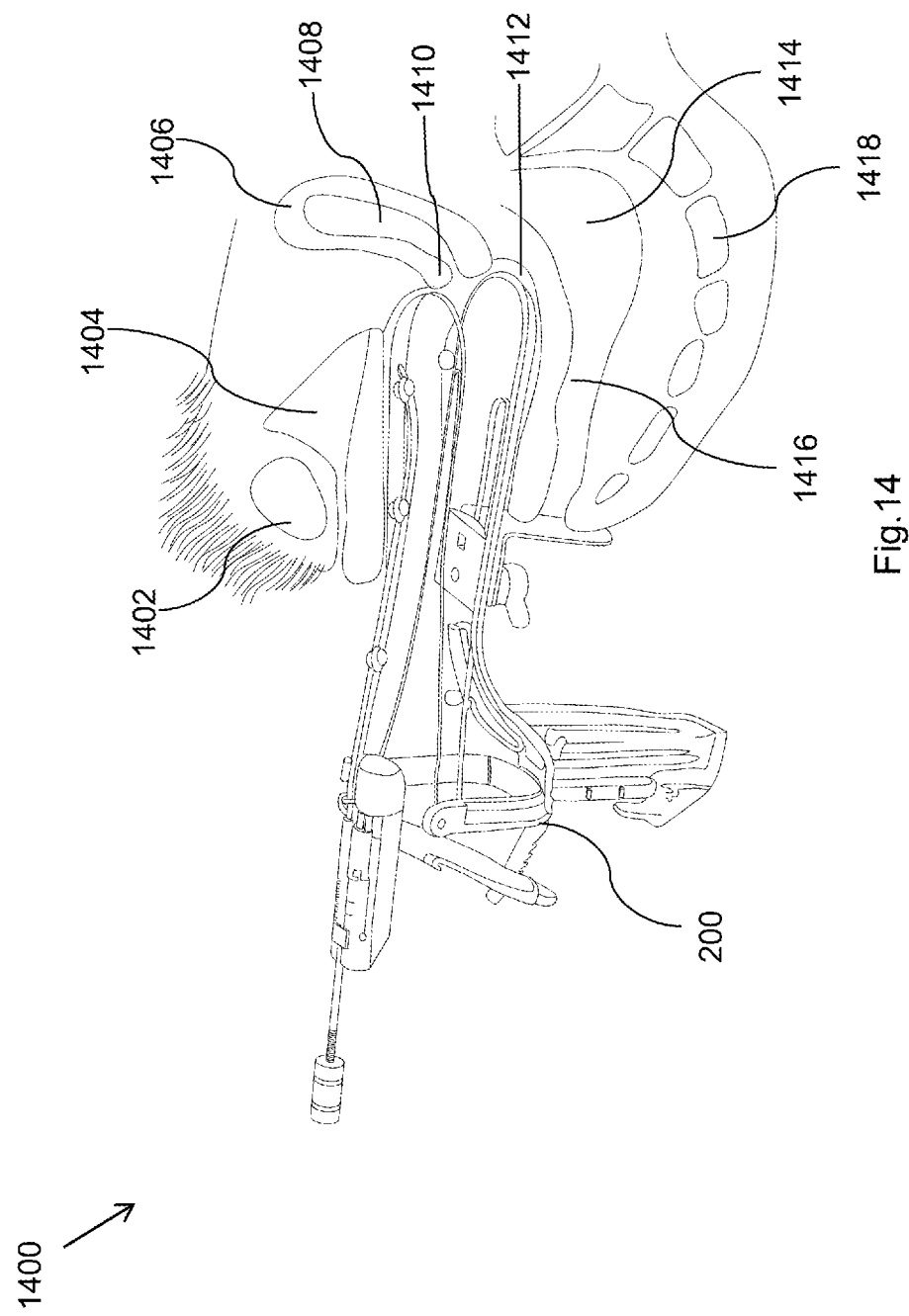
FIG. 14 illustrates a medical device inserted into a body opening, in accordance with an embodiment of the present invention.

FIG. 14 illustrates the medical device 200 of FIG. 2 inserted into a body opening. As shown, the body opening is the vagina of a patient. In accordance with various other embodiments, the body opening may be an anal canal. Referring to FIG. 14, the anatomy of the pelvic region, including a pubic bone 1402, a bladder 1404, a uterus 1406, a uterine cavity 1408, a cervix 1410, a vaginal canal 1412, a rectum 1414, an anal canal 1416, and a spine 1418, is depicted.

Figure 15:
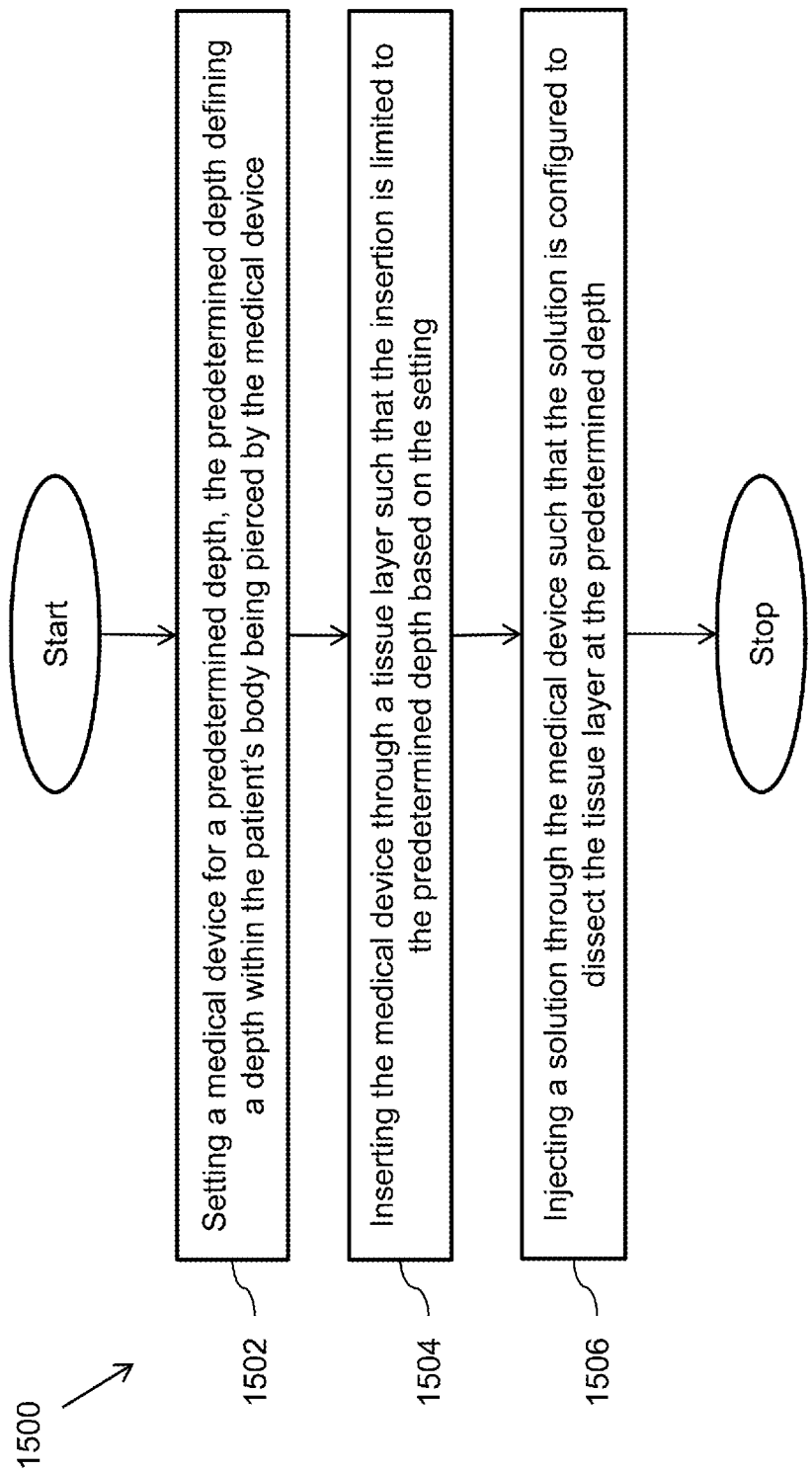
FIG. 15 illustrates a flowchart depicting a method for dissecting a tissue layer in a patient' body, in accordance with an embodiment of the present invention.

FIG. 15 illustrates a flowchart depicting a method 1500 for dissecting a tissue layer of a patient's body. The present invention allows dissection of the tissue layer to a predetermined depth using a medical device such as the medical device 200. The medical device 200 includes the insertion member 202, needle member 204, and the adjustment member 206 as described in conjunction with FIG. 2. The predetermined depth is controlled and adjusted by the adjustment member 206. A saline solution is passed through the needle member 204 to dissect the tissue layer and create a pocket therein at the predetermined depth. The medical device 200 further includes a syringe such as the syringe 1300 configured to pass the saline solution through the needle member 204.

Referring to FIGS. 2, 14 and 15, the surgical procedure for dissecting the tissue layers is described herein. In accordance with an exemplary embodiment, the medical device 200 is used hereafter to describe the surgical procedure; however, in certain other embodiments, the medical device 100 may also be employed.

The method of dissection includes setting the medical device for the predetermined depth at step 1502. The predetermined depth defines a depth within the patient's body being pierced by the medical device 200. The medical device 200 is set by the adjustment member 206. In some embodiments, the adjustment member 206 is configured to move between a first position and a second position with respect to the insertion member 202 or the adjustment member support 402 for setting to the predetermined depth. In accordance with various embodiments, the adjustment member 206 can include various types of mechanisms for adjusting the value of the predetermined depth. In some embodiments, the adjustment member 206 includes an adjustment screw 406 and a nut 408 such that the movement of the adjustment screw 406 between the first position and the second position (with respect to the insertion member 202 or the adjustment member support 402) will cause an adjustment in the value of the predetermined depth accordingly. In some other embodiments, various other types of mechanisms for moving the adjustment member 206 between the first and the second position can be employed. In accordance with various embodiments, the adjustment screw may include a lumen such that the needle member 104 can extend through the adjustment screw via the lumen. The adjustment member 106 may further include a stopper to limit advancement of the needle member 104 within the lumen to a certain extent only. The needle member 104 may include a projection or any similar kind of expanded portion such that the projection abuts the stopper when the needle member 104 extends through the lumen of the adjustment member 106, thereby limiting advancement of the needle member 104 within the lumen. The adjustment member 206 has further been described in conjunction with FIG. 2. The predetermined depth of insertion achieved by setting can be displayed to an operator on a scale such as the scale 416 illustrated in FIG. 4.

The method further includes inserting the medical device 200 through the tissue layers at step 1504, such that the insertion is limited to the predetermined depth based on setting of the medical device 200. In embodiments, the needle member 204 of the medical device 200 pierces through the tissue layers to the predetermined depth. In this manner, the insertion process can be controlled by the operator and harmful side-effects such as bladder or urethra perforation can be avoided.

As discussed in conjunction with FIG. 2, the distal end portion 226 of the needle member 204 is inclined with respect to the distal end portion of the upper blade member 208b of the insertion member 202 by an angle Ø. Therefore, during insertion, the needle member 204 advances through a vaginal wall of the patient at a certain angle. In accordance with various embodiments, the insertion of the medical device 200 can be performed through any of the surgical processes currently used such as trans-vaginal or through the abdomen.

At step 1506, a solution is injected through the medical device 200 such that the solution is configured to dissect the tissue layers at the predetermined depth. The step of injecting the solution is performed after the operator has ensured that the predetermined depth has been reached and tip portion of the needle member 204 sits at a position intended for dissection. Subsequently, the solution is injected by a syringe such as the syringe 1300 as described in conjunction with FIG. 13. The solution is passed through a lumen defined along the length of the needle member 204 that is coupled to the syringe 1300 at its proximal end portion. In some embodiments of the present invention, the solution contained in the syringe 1300 is saline and can be pushed through the needle member 204 when required. The volume of the solution can vary as per the requirements and the operator can decide based on his experience. In some embodiments, the volume of the solution can range between 0.5 ml and 5 ml. The solution is used for hydro-dissecting the tissue layer. Since the depth is pre-determined, the saline solution will reach the bodily tissues only at the predetermined depth, thereby creating a hydro-dissecting pocket.

In some embodiments, the step of injecting the solution can be performed multiple times to create multiple hydro-dissecting pockets one beside the other at different locations such that a hydro-dissecting plane is formed in between the vagina and the bladder. In this scenario, for example, the medical device 200 is inserted into the body opening to a first location as shown in FIG. 14. The needle member 204 is then advanced to a first predefined depth and the solution is injected for dissection. Subsequently, the needle member 204 is withdrawn and the medical device 200 is moved to a second location inside the body opening such that the second location is different than the first location. The second location may be further in the posterior end of the vagina. The needle member 204 is again advanced to a second predefined depth and the solution is injected for dissection at the second location. Subsequently, the needle member 204 is withdrawn and the medical device 200 is removed from the body opening. The first predefined depth and the second predefined depth can be same or different. Similarly, more pockets may be created at various other locations.

After the injection of the solution for hydro-dissecting the tissue layers, the medical device 200 can be taken out and manual incisions for surgery can be made. In some embodiments, the incisions made are about 0.5 cm to 4 cm in length depending on the nature of the surgery. As the tissue layers are already hydro-dissected at the predetermined depth, the solution may leak out when the operator reaches the tissue layers at the predetermined depth during the surgery. And thus, the operator may identify the appropriate depth that he needs to work at.

In accordance with some embodiments, a guidewire (not shown in the figures) can be inserted through the lumen of the needle member 204. The guidewire can be a kind of wire or any wire-like member having a defined length and configured to provide strength to the needle member 204. The guidewire is disposed in the lumen of the needle member 204 after the insertion member 202 and the needle member 204 are placed inside the body opening such as the vaginal canal. Thereafter, the needle member 204 is inserted into the tissue layer as described above with the guidewire in the lumen. Subsequently, after the tissue layer is pierced to the predetermined depth, the guidewire is removed from the lumen and the solution is injected as described above. The use of guidewire may help in preventing bending of the needle member 204 beyond a certain limit.

In accordance with some embodiments, the method may also include adjusting the lock assembly 214 to limit and/or make adjustments to the depth of insertion of the insertion member 202 in the patient's body opening such as a vagina, anal canal, and the like. Therefore, the insertion member 204 is inserted only to a defined depth inside the body opening once the insertion member is locked through the lock assembly 214.

As described in conjunction with FIG. 1, the method of dissection of the tissue layers can be assisted by using a video camera and/or a light source coupled to the medical device 200.

In accordance with various embodiments, the dissection of the tissue layers as described above in conjunction with various figures is performed to prepare the bodily tissues for receiving a bodily implant. The bodily implant can be a sling, a mesh-based device, and the like that can be placed in the bodily tissues at a place where a hydro-dissected pocket or hydro-dissected plane is created. Thus, the hydro-dissected pocket/plane provides a space for receiving the bodily implant.

In some embodiments, a medical device includes a needle, an adjustment member and an adjustment member support. The needle member is configured to be inserted into a tissue layer. The needle member has a proximal end portion and a distal end portion. The adjustment member is coupled to the proximal end portion of the needle member. The adjustment member includes an adjustment screw and a nut for setting a predetermined depth of insertion of the needle member within the tissue layer. The adjustment member support is configured to provide a support to the adjustment screw and the nut. The adjustment screw is configured to move between a first position and a second position with respect to the adjustment member support to limit insertion of the needle member within the tissue layer to the predetermined depth.

In some embodiments, a syringe is removably coupled to the needle member and contains a solution. The syringe is configured to inject the solution through the needle member causing creation of a pocket in the tissue layer proximate the distal end portion of the needle member.

In some embodiments, the needle member is a surgical needle. In some embodiments, the solution is a saline solution. In some embodiments, the pocket is created in the tissue layer by hydro-dissection technique. In some embodiments, the adjustment member further comprises a scale for locating a pre-settable numerical value of the predetermined depth. In some embodiments, the adjustment member further comprises a stopper configured to stop the needle member from being advanced past the predetermined depth into the tissue layer. In some embodiments, a video camera is configured to assist an operator in monitoring the tissue layer during dissection. In some embodiments, a light source is configured to assist an operator during insertion of the needle member. In some embodiments, a guidewire is disposed within a lumen defined by the needle member. The guidewire is configured to provide strength to the needle member.

In some embodiments, a medical device includes an insertion member, a needle member, and an adjustment member. The insertion member is configured to be inserted into a body opening. The insertion member has an expandable portion configured to expand and collapse. The needle member is coupled to the insertion member and is configured to be inserted into a tissue layer. The needle member has a proximal end portion and a distal end portion. The adjustment member is coupled to the proximal end portion of the needle member and is configured to limit advancement of the insertion member within the tissue layer to a predetermined depth.

In some embodiments, a syringe is removably coupled to the needle member and contains a solution. The syringe is configured to inject the solution through the needle member causing creation of a pocket in the tissue layer proximate the distal end portion of the needle member. In some embodiments, the insertion member is a vaginal speculum. In some embodiments, the distal end portion of the needle member is curved to a defined length thereby defining an angle with respect to the insertion member. In some embodiments, the angle measure varies between 30-45 degrees. In some embodiments, the adjustment member comprises an adjustment screw for setting the predetermined depth. In some embodiments, the adjustment member further comprises a scale for locating a pre-settable numerical value of the predetermined depth. In some embodiments, the adjustment member further comprises a stopper configured to stop the needle member from being advanced past the predetermined depth into the tissue layer.

In some embodiments, a method for dissecting a tissue layer of a patient's body includes setting a medical device having a needle member and an adjustment member for a predetermined depth, the predetermined depth defining a depth within the tissue layer of the patient's body being pierced by the needle member; inserting the needle member through the tissue layer such that the insertion is limited to the predetermined depth; and injecting a solution through the needle member such that the solution is configured to dissect the tissue layer at the predetermined depth.

In some embodiments the method includes adjusting a depth of insertion of the medical device within a body opening. In some embodiments, the method includes inserting a guidewire within a lumen defined by the needle member, the guidewire configured to provide strength to the needle member.

In some embodiments, the needle member is a surgical needle.

In some embodiments, the method includes removing a guidewire after inserting the needle member and prior to injecting the solution for dissection of the tissue layer.

In some embodiments, the setting of the medical device comprises adjusting an adjustment screw for the predetermined depth.

In some embodiments, the method includes placing a bodily implant in the dissected tissue layer.

In some embodiments, the bodily implant is a sling.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device comprising:
an insertion member configured to be inserted into a body opening, the insertion member having a first blade member and a second blade member, each of the first blade member and the second blade member having a proximal end portion and a distal end portion, wherein the first blade member and the second blade member are movably coupled to each other at their proximal end portions, the distal end portion of the first blade member defining an opening through a thickness of the first blade member, the first blade member having a first surface and a second surface, the first surface being separated from the second surface by the thickness;
a needle member configured to be inserted into a tissue layer, the needle member having a proximal end portion and a distal end portion, the needle member being coupled to the first blade member, the needle member having a portion that extends along the first surface of the first blade member and slidably coupled to the first surface of the first blade member, and a curved portion that extends through the opening on the distal end portion of the first blade member, the curved portion of the needle member extending upward through the first blade member via the opening and curving away from the second surface of the first blade member; and
an adjustment member coupled to the proximal end portion of the needle member, the adjustment member comprising:
an adjustment screw and a nut for setting a predetermined depth of insertion of the needle member within the tissue layer; and
an adjustment member support configured to provide a support to the adjustment screw and the nut,
wherein the adjustment screw is configured to move between a first position and a second position with respect to the adjustment member support to limit insertion of the needle member within the tissue layer to the predetermined depth.

2. The medical device of claim 1 further comprising a syringe removably coupled to the needle member and containing a solution, the syringe configured to inject the solution through the needle member causing creation of a pocket in the tissue layer proximate the distal end portion of the needle member.

3. The medical device of claim 2, wherein the solution is a saline solution.

4. The medical device of claim 2, wherein the pocket is created in the tissue layer by hydro-dissection technique.

5. The medical device of claim 1, wherein the needle member is a surgical needle.

6. The medical device of claim 1, wherein the adjustment member further comprises a scale for locating a pre-settable numerical value of the predetermined depth.

7. The medical device of claim 1, wherein the adjustment member further comprises a stopper configured to stop the needle member from being advanced past the predetermined depth into the tissue layer.

8. The medical device of claim 1 further comprising a video camera configured to assist an operator in monitoring the tissue layer during dissection.

9. The medical device of claim 1 further comprising a light source configured to assist an operator during insertion of the needle member.

10. The medical device of claim 1 further comprising a guidewire disposed within a lumen defined by the needle member, the guidewire being configured to provide strength to the needle member.

11. The medical device of claim 1, wherein the needle member is slidably coupled to the first surface of the blade number with a plurality of brackets.

12. A medical device comprising:
an insertion member configured to be inserted into a body opening, the insertion member having a first blade member and a second blade member, each of the first blade member and the second blade member having a proximal end portion and a distal end portion, wherein the first blade member and the second blade member are movably coupled to each other at their proximal end portions, the distal end portion of the first blade member defining an opening through a thickness of the first blade member, the first blade member having a first surface and a second surface, the first surface being separated from the second surface by the thickness;
a needle member coupled to the first blade member of the insertion member and configured to be inserted into a tissue layer, the needle member having a proximal end portion and a distal end portion, the needle member having a portion that extends along the first surface and slidably coupled to the first surface of the first blade member, and a curved portion that extends through the opening on the distal end portion of the first blade member, the curved portion extending upward through the first blade member and forming an angle with the second surface of the first blade member; and
an adjustment member coupled to the proximal end portion of the needle member and configured to limit advancement of the insertion member within the tissue layer to a predetermined depth.

13. The medical device of claim 12 further comprising:
a syringe removably coupled to the needle member and containing a solution, the syringe configured to inject the solution through the needle member causing creation of a pocket in the tissue layer proximate the distal end portion of the needle member.

14. The medical device of claim 12, wherein the insertion member is a vaginal speculum.

15. The medical device of claim 12, wherein the adjustment member includes an adjustment screw and a nut for setting the predetermined depth, the adjustment screw defining a lumen, the needle member extending through the lumen of the adjustment screw.

16. The medical device of claim 12, wherein the angle is between 30-45 degrees.

17. The medical device of claim 12, wherein the adjustment member comprises an adjustment screw for setting the predetermined depth.

18. The medical device of claim 12, wherein the adjustment member further comprises a scale for locating a pre-settable numerical value of the predetermined depth.

19. The medical device of claim 12, wherein the adjustment member further comprises a stopper configured to stop the needle member from being advanced past the predetermined depth into the tissue layer.

20. The medical device of claim 12, wherein the needle member is slidably coupled to the first surface of the blade number with a plurality of brackets.

* * * * *